US00PP21350P3

(12) United States Plant Patent
Goff

(10) Patent No.: US PP21,350 P3
(45) Date of Patent: Sep. 28, 2010

(54) **VARIETY OF *CANNA* PLANT NAMED 'LON01'**

(50) Latin Name: *Canna hybrida*
Varietal Denomination: LON01

(75) Inventor: Gregory Benjamin Goff, Guadalajara (MX)

(73) Assignee: Sofia R. Villasenor Urrea, Guadalajara (MX)

( * ) Notice: Subject to any disclaimer, the term of this patent is extended or adjusted under 35 U.S.C. 154(b) by 1006 days.

(21) Appl. No.: 11/416,520

(22) Filed: May 3, 2006

(65) Prior Publication Data

US 2007/0261144 P1 Nov. 8, 2007

(51) Int. Cl.
*A01H 5/00* (2006.01)

(52) U.S. Cl. ..... Plt./415

(58) Field of Classification Search ..... Plt./415
See application file for complete search history.

*Primary Examiner*—Kent L Bell
(74) *Attorney, Agent, or Firm*—Fulwider Patton LLP

(57) ABSTRACT

A new and distinct cultivar of *Canna* plant named 'LON01' characterized by browned burgundy leaves tending to olive green as the leaf ages.

2 Drawing Sheets

BACKGROUND OF THE NEW PLANT

The present invention comprises a new and distinct cultivar of *Canna*, botanically known as *Canna hybrida* and further known by the varietal name 'LON01' and the trade name 'Tropicanna Black.' The new variety was discovered through a selective breeding program by Greg Goff at Av. Union 274-A, Col. Americana, Guadalajara, Jalisco Mexico 44100. The seedlings were selected on Aug. 21, 2001, and the new variety is a product of open pollination. The pollination took place in a group of *cannas* and 'LON01' was the resultant seedling discovered in this population, where the seedling was collected from the group of *Cannas* including 'Yellow King Humbert' (unpatented), 'North Star Landscape Red' (unpatented), 'Crimson Beauty' (unpatented), 'Rose Futurity' (unpatented), 'President' (unpatented), and 'Angel Pink Beauty' (unpatented). The new cultivar was selected from the progeny by the inventor Greg Goff at Av. Union 274-A, Col. Americana, Guadalajara, Jalisco Mexico 44100.

SUMMARY OF THE INVENTION

The new variety is the result of a selective breeding program taken from the breeder's collection of unique and interesting seedlings in the Nursery at Av. Union 274-A, Col. Americana, Guadalajara, Jalisco Mexico 44100 in the year 2001. These seedlings were selected and propagated through rhizome divisions selecting for differences in color variation of the interveinal striping.

The new cultivar has since been asexually reproduced by rhizome divisions at Silvan, Victoria, Australia and has been repeatedly asexually reproduced. Continued observations from the vegetative divisions have confirmed that the distinguishing features of this new cultivar came true, remain stable and are retained through successive propagation.

A comparative trial of the new cultivar with its closest known variety 'Phasion', trade name "Tropicana" was conducted at Clyde, VIC, Australia in February 2006, in a garden environment. The results of the comparative trial is provided below:

TABLE 1

Comparison with Other Cultivars

| | Flower Color | Leaf Color |
|---|---|---|
| 'Phasion' | Orange | Variegated |
| 'Rose Futurity' | Coral Pink | |
| 'Crimson Beauty' | Red | Green |
| 'North Star Landscape Red' | Cerise Red | Green |
| 'Lon01' | Orange-Red | Burgundy |

BRIEF DESCRIPTION OF THE DRAWINGS

The accompanying photographs illustrates the new cultivar, the color being as nearly true as possible with color photographs of this type, where.

DETAINED BOTANICAL DESCRIPTION OF THE NEW PLANT

Figure 1:
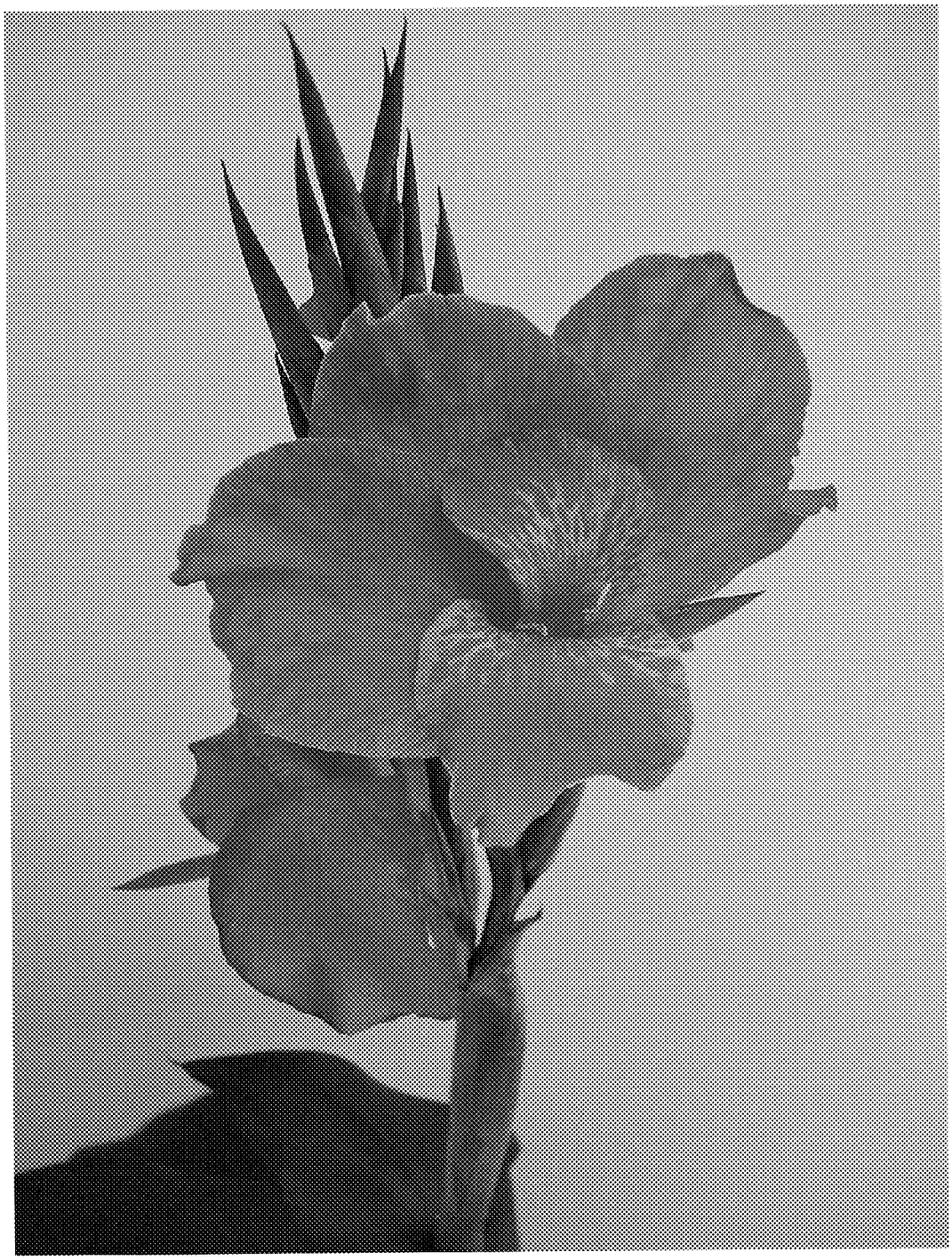
FIG. 1 depicts a six month old plant in a pot and FIG. 2 is a close-up view of the flower.
Figure 2:
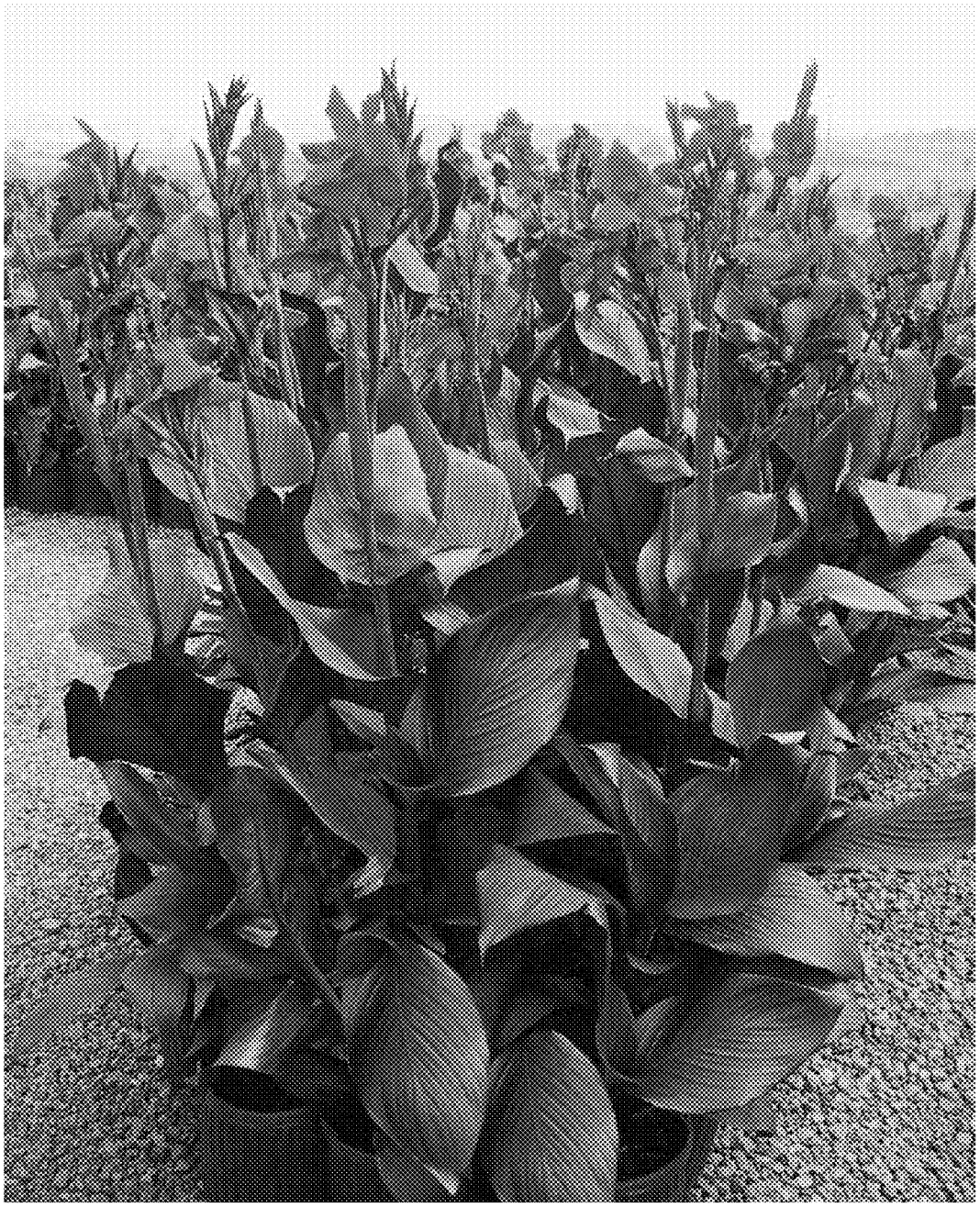

The following detailed description sets forth characteristics of the new cultivar at approximately six months. The data which defines each characteristic was collected from the comparative trial identified above, using R.H.S. color cards issued in 1995.

THE PLANT

Classification:

*Botanical.*—*Canna hybrida.*

*Commercial.*—'LON01'.

*Origin.*—Selected seedling.

*Propagation.*—Rhizome division.

Form:

*Type.*—Dense, upright mass of stems topped by flowering panicles, slowly expanding in width by rhizomes beneath the soil surface.

*Height.*—Up to 1500 mm.

*Width.*—Up to 500 mm.

*Growth rate and habit*.—Flowers in first season from Summer to well into Autumn. Flower truss lasts approximately two weeks, each individual floret lasting two to three days.
*Strength*.—Free standing.

Stem:
*Length*.—180–200 cm.
*Diameter*.—28 mm at base.
*Color*.—RHS N186C.

Leaves:
*Arranged*.—Spirally.
*Shape*.—Lamina is large, broad, ovate and elliptic, with prominent venation with deep veins and long midrib.
*Apex*.—Acute.
*Base descriptors*.—Sheathed.
*Length*.—Mean 560 mm.
*Width*.—Mean 233 mm.
*Margin*.—Entire.
*Texture*.—Thick, smooth but with prominent rib structure, and somewhat waxy feel.

Color:
*Upper*.—The predominant leaf color is RHS 220A with a burgundy hue (on juvenile leaf); As leaf matures, it becomes more green, RHS 147A (closest available).
*Lower*.—The predominant leaf color is RHS 220A with a burgundy hue (on juvenile leaf); As leaf matures, it becomes more green, RHS 147A (closest available).
*Venation*.—Pinnate.

MATURE INFLORESCENCE

General:

Bud:
*Shape*.—Lanceolate — gladiolus like (elongated spikes).

Sepal:
*Quantity*.—3.
*Apex*.—Acute.
*Margin descriptors*.—Incurled, smooth.
*Color*.—Innerside is RHS 10B; secondary color is RHS N34A; outerside is RHS N34A.
*Length*.—75 mm.
*Width*.—22 mm.
*Form*.—Resembles petal although completely rolled.

Petals: Time of flowering is first season from Summer to well into Autumn. The flower truss lasts approximately 2 weeks, each individual floret lasts 2–3 days.
*Quantity*.—5.
*Shape*.—Ovate.
*Apex*.—Rounded.
*Base descriptors*.—Cordate.
*Margin descriptors*.—Slight undulation.
*Size*.—Medium.
*Arrangement*.—Overlapping.
*Length*.—75–90 mm.
*Width*.—50–60 mm.

Roots:
*Type*.—Rhizomes.
*Color*.—Midzone outside — Red Orange Group RHS42B. Midzone inside — Red Orange Group RHS33B. Margin inside — Red Orange Group RHS33B.

Flowers:
*Quantity*.—15–30.
*Size*.—Floret medium.
*Profile upper*.—Flattened Concave.
*Profile lower*.—"V" shaped.
*Color*.—RHS 33A.

Floret:
*Length*.—Approximately 80 mm (fully open floret).
*Width*.—95–110 mm.

Pedicel:
*Length*.—Peduncle spike approximately 300 mm.
*Diameter*.—11 mm at widest point.
*Color*.—RHS 187B.

Fragrance: None detected

Persistence:
*Disease resistance*.—Very tolerant.
*Lasting quality*.—Regenerating.

Length of flowering period:
*Med, long*.—Medium.

Color midzone outside: 42B RHS
Color midzone inside: 33 B RHS
Color margin inside: 33B RHS
Color basal spot: Yellowish white

REPRODUCTIVE ORGANS

Stamens: Modified petal, 1 per floret, single, shape is lobed

Filaments:
*Color*.—light yellow to white.

Anther: Orange

Pistils:
*Style*.—Cream.
*Shape*.—Flattened lobed shaped blade of orange-red, length 70 mm.
*Quantity*.—1 per floret.

Seed vessel: Medium, tri-lobed, spiky anemone like

Size:
*Color*.—Predominantly RHS 187B; secondary RHS 138D.

Seed: Small, ball-shaped, attached to center pier, approximately 8 to vessel

Tolerances: Sensitive to frost

GENERAL CHARACTERISTICS

The varietal is characterized by large, broad leaves having undulations of margin that are strong in juvenile becoming weak with age. Reflexion of margin is absent, and venation is deeply indented. The predominant color is browned burgundy (RHS 187A), lateral venations are raised. The aspect is upright, as the leaves unfurl as they grow from the stalk. As the leaf ages, the browned burgundy tends to olive green (147A), with the color consistent on the lower and upper sides. For each growth spike, one to three umbels are present flowering first at the apex, second below first peduncle, and third from a lower leaf axil. The varietal flowers in the first season from Summer to well into Autumn, where each flower lasts approximately two weeks and each floret lasts 2–3 days.

I claim:

1. A new and distinct variety of *Canna* plant, substantially as shown and described.

* * * * *